United States Patent [19]

Oyama et al.

[11] Patent Number: 4,622,125

[45] Date of Patent: Nov. 11, 1986

[54] OXYGEN CONCENTRATION CONTROL SYSTEM

[75] Inventors: Yoshishige Oyama; Tadashi Kirisawa, both of Katsuta; Minoru Osuga, Hitachi, all of Japan

[73] Assignee: Hitachi, Ltd., Tokyo, Japan

[21] Appl. No.: 653,550

[22] Filed: Sep. 24, 1984

Related U.S. Application Data

[63] Continuation of Ser. No. 483,173, Apr. 8, 1983, abandoned.

[30] Foreign Application Priority Data

Apr. 12, 1982 [JP] Japan .................................. 57-59676
Nov. 4, 1982 [JP] Japan ................................. 57-192412

[51] Int. Cl.$^4$ .......................................... G01N 27/58
[52] U.S. Cl. ..................... 204/406; 60/276; 123/489; 204/425
[58] Field of Search ................... 204/406, 425, 426; 123/489; 60/276

[56] References Cited

U.S. PATENT DOCUMENTS

| | | | |
|---|---|---|---|
| 3,616,274 | 10/1971 | Eddy | 204/1 T |
| 3,650,934 | 3/1972 | Hickham et al. | 204/412 |
| 3,907,657 | 9/1975 | Heijne et al. | 204/406 |
| 3,990,411 | 11/1976 | Toelle et al. | 123/489 |
| 4,158,166 | 6/1979 | Isenberg | 204/1 T X |
| 4,181,944 | 1/1980 | Yamauchi et al. | 364/431 |
| 4,272,331 | 6/1981 | Hetrick | 204/1 T |
| 4,287,865 | 9/1981 | Seitz | 123/489 |
| 4,366,039 | 12/1982 | Uchida et al. | 204/406 |
| 4,375,796 | 3/1983 | Ohgami et al. | 123/440 |
| 4,402,292 | 9/1983 | Ohgami et al. | 123/440 |

*Primary Examiner*—G. L. Kaplan
*Attorney, Agent, or Firm*—Antonelli, Terry & Wands

[57] ABSTRACT

An oxygen concentration control system comprising an electrolyte of the oxygen-ionconduction type exposed on its one surface to the interior of a chamber conducting gases under measurement through a diffusion resistance member, and the system controls the oxygen concentration of gases so that the voltage created across the electrolyte is equal to the predetermined voltage. The inventive system comprises a means for preventing the malfunctioning of the control system caused by the time lag in sensing the oxygen concentration which occurs when the oxygen concentration of the gases varies abruptly or the setting of the oxygen concentration is varied.

12 Claims, 18 Drawing Figures

OXYGEN CONCENTRATION CONTROL SYSTEM

This is a continuation of application Ser. No. 483,173, filed Apr. 8, 1983 and now abandoned.

The present invention relates to an oxygen concentration control system using oxygen-ion-conductive solid electrolyte and, particularly, to an oxygen concentration control system suitable for use in combustion devices, such as internal combustion engines.

In the conventional oxygen concentration sensor, if the oxygen concentration of gases under measurement varies rapidly or if the setting of the oxygen concentration is varied abruptly, the oxygen concentration sensor detects the oxygen concentration of the gases with a time lag caused by the diffusion of oxygen within the gas conduit to the oxygen concentration sensor, and a time lag caused by the diffusion of oxygen ions within the electrolyte, particularly, a time lag due to the recharging of oxygen ions to the electrolyte when the electrolyte provides electron conduction. This causes a degraded response in the oxygen concentration control system for gases under measurement. In addition, due to the delay of detection by the oxygen concentration sensor, the detected oxygen concentration does not coincide with the actual oxygen concentration of gases, resulting possibly in a malfunctioning of the control system.

Accordingly, it is an object of the present invention to provide an oxygen concentration controller which prevents the inferior response to the variation of the oxygen concentration in gases under measurement.

Another object of the present invention is to provide an oxygen concentration controller which prevents malfunctioning of control caused by the variation of the oxygen concentration in gases under measurement.

According to one embodiment of the present invention, the electrolyte of the oxygen sensor is supplied with a certain magnitude of electric current, and when the sensor provides an output voltage in excess of a predetermined voltage, oxygen is supplied to the gas conduit upstream of the sensor, whereby the oxygen concentration of the gases is controlled.

According to another embodiment of the present invention, when the oxygen concentration of gases under measurement has varied, the operation of the oxygen concentration control system is halted for a certain duration.

The above and other objects, features and advantages of the invention will be apparent from the following detailed description taken in conjunction with the accompanying.

Figure 1:
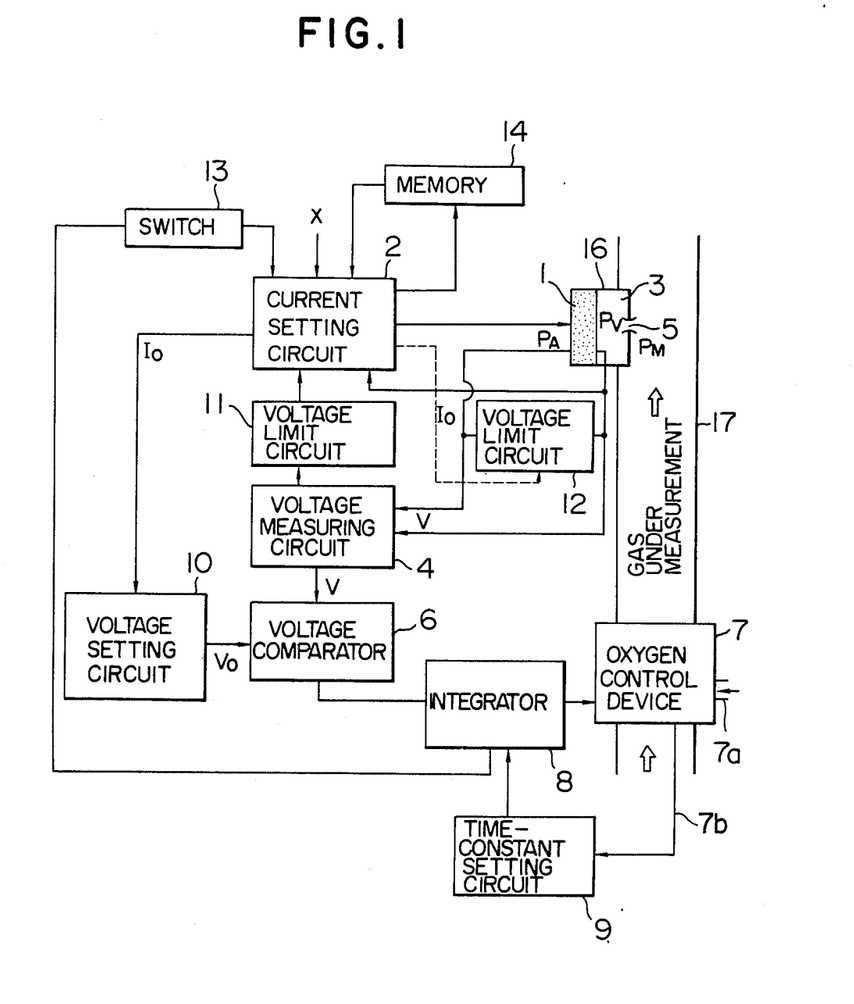
FIG. 1 is a block diagram showing one embodiment of the inventive oxygen concentration control system.

In FIG. 1, an oxygen concentration sensor 16 consisting of a solid electrolyte 1, a chamber 3 and a diffusion resistance member 5 is provided within a measurement gas conduit 17. The solid electrolyte 1 is of the oxygen-ion-conduction type formed of a mixture of $Z_rO_2$-$Y_2O_3$ in the shape of a disc having dimensions of 10 mm in diameter and 2 mm in thickness. The electrolyte 1 has on its opposing sides porous platinum electrodes, which are connected to a current setting circuit 2. The circuit 2 may be of any type, such a pulse current source, capable of supplying a variable effective current to the electrolyte 1. The chamber 3 has a volume of $4 \times 10^{-3}$ cm$^3$, and is located on the right side of the electrolyte 1, as seen in FIG. 1. The chamber 3 communicates with the measurement gas conduit 17 through an orifice (0.5 mm in diameter and 2 mm in length) or through the diffusion resistance member 5 made of porous ceramic or the like. There is provided a voltage measuring circuit 4 which measures the voltage difference V across the electrolyte 1. The circuit 4 has a measuring range of around 0–2 volts, and its output V is supplied to a voltage comparator 6. The output of the comparator 6 is fed through an integrator 8 to an oxygen control device 7 which is provided within the measurement gas conduit 17 upstream of the sensor 16. The integrator 8 is controlled for its operating time-constant by a time-constant setting circuit 9. The comparator 6 receives at its other input the output voltage Vo from a voltage setting circuit 10. There are further provided a voltage limiters 11 and 12 which control the voltage of the electrolyte 1, as well as a switch 13 and a memory 14.

The arrangement of FIG. 1 operates as follows.

When the current setting circuit 2 supplies a current I to the electrolyte 1, the voltage measuring circuit 4 provides a voltage V. The voltage V can be expressed as a function of the resistance r of the electrolyte 1, the temperature T of the electrolyte, the oxygen partial pressure $P_A$ on the opposite side of the electrolyte from the chamber 3 ($P_A$ is proportional to the oxygen concentration), and the oxygen partial pressure $P_V$ in the chamber 3:

$$V = rI + \frac{RT}{4F} \ln \frac{P_A}{P_V} \tag{1}$$

where R is the gas constant and F is the Faraday constant.

On the other hand, the current I can be expressed as a function of the partial pressure $P_M$ in the exterior of the diffusion resistance member 5, and the oxygen partial pressure $P_V$:

$$I = \frac{Da \cdot 4F}{l \cdot RT} (P_M - P_V) \tag{2}$$

where D is the diffusion factor, a is the cross section of the diffusion resistance member 5, and l is the length of the diffusion resistance member 5.

Figure 2:
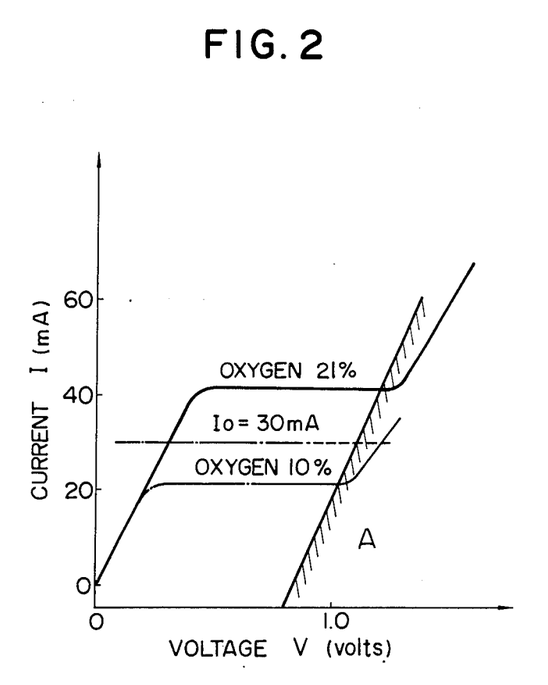
FIGS. 2 to 5 are graphical representations explaining the operation of the system shown in FIG. 1.

From the above relations it will be understood that as the current I increases, the voltage V given by Equation (1) increases, and at the same time the partial pressure $P_V$ in Equation (2) decreases provided that the partial pressure $P_M$ is constant. The above I vs. V relationship is shown in FIG. 2.

As the current further increases, the partial pressure $P_V$ in Equation (2) approaches zero. In this case, the voltage in Equation (1) rises sharply and from the relationship of Equation (2), it is seen that the current can no longer be increased. In other words, as the voltage V increases the current I created by oxygen ions in the electrolyte 1 increases proportionally, as shown in FIG. 2, but as the oxygen partial pressure $P_V$ in the chamber 3 approaches zero, oxygen ions cannot be supplied into the electrolyte 1, resulting in a limitation of the current I. In general, with the voltage V around 0.2 volt, the partial pressure $P_V$ falls to a near-zero range of around $10^{-12}$. When the voltage V exceeds 1 volt, electron conduction is added to oxygen ion conduction, and the current increases in proportion to the voltage V as shown in the hatched portion A in FIG. 2. The higher the oxygen concentration of gases under measurement, the greater will be the quantity of oxygen to diffuse through the diffusion resistance member 5 into the chamber 3, and the limit of current I goes to a higher level as shown in FIG. 2. Accordingly, the current limit Io is determined depending on the oxygen concentration.

When the current I is set to a certain value Io by the current setting circuit 2 and the oxygen concentration of the measurement gas is varied, the voltage V varies sharply at an oxygen concentration corresponding to the current limit Io. A voltage Vo which resides in the center of the variation range is set by the voltage setting circuit 10. The voltage V detected across the electrolyte 1 is compared with the setup voltage Vo by the voltage comparator 6, and the oxygen control device 7 controls the oxygen concentration of the measurement gas so that the application voltage V coincides with the setup voltage Vo. Thus, control proceeds so that gases with the oxygen concentration corresponding to the current limit Io is produced.

In this control system, a slight increase in $P_M$ causes an increase of $P_V$, that results in an enhanced oxygen-ion-conduction, and the voltage V will fall sharply. Conversely, when $P_M$ falls slightly, the diffusion of oxygen through the resistance member 5 into the chamber 3 decreases because of the control for $P_V$ to the near-zero range, and the voltage V rises sharply in order to maintain the current at Io, and this is fulfilled by electron conduction.

Figure 3:
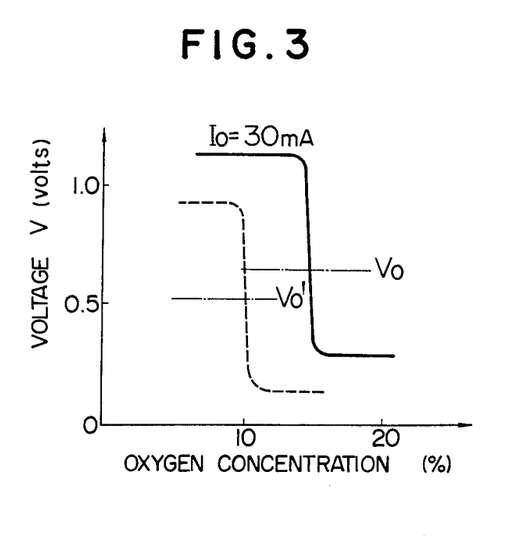
Figure 4:
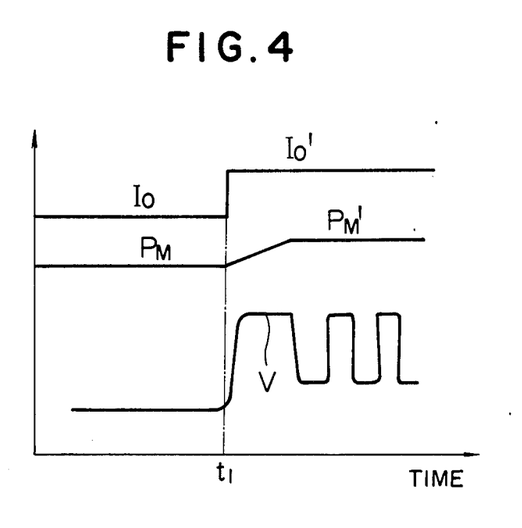

Since the voltage V responds sharply to the variation of the oxygen concentration, as shown in FIG. 3, the control device 7 is controlled in a PI control mode through the integrator 8, thereby preventing a hunting in controlling the oxygen concentration in the measurement gas. In order to achieve an optimal control, the time-constant of the integrator 8 is varied by the time-constant setting circuit 9''; in response to the signal on line 7b indicative of the flowrate of gases as determined by a flow meter (not shown) in the oxygen control device 7.

As shown in Equation (1), the voltage V includes the rI component, and if the current Io set by the current setting circuit 2 is varied, the voltage variation range is moved as shown by the dashed line in FIG. 3. On this account, the setup voltage Vo is varied as shown by Vo' by the voltage setting circuit 10 in response to the variation of Io thereby to achieve an optimal control.

The target oxygen concentration of gases can be changed by application of an external control signal x to the current setting circuit 2 so as to vary the current Io. In particular, for increasing the target oxygen concentration ($P_M$), the current Io is first brought to an increased level Io'. Then, $P_M$ decreases below the level corresponding to the current Io', causing the voltage V to increase, and the control device 7 operates to increase $P_M$. When $P_M$ increases to $P_M'$ which corresponds to Io', $P_V$ increases and the voltage V falls to Vo. Since the V includes the rI component, the constant voltage Vo will not provide a satisfactory control, and this problem is avoided by varying the voltage Vo in response to the current Io. As mentioned previously, provision of a constant Io or too small a partial pressure $P_V$ is apt to drive the control into the domain of electron conduction. Once the system enters the electron conduction domain, there are few oxygen ions within the electrolyte 1, and in restoring oxygen-ion-conduction, the electrolyte is first filled with oxygen ions and then the current created by oxygen ions will flow, resulting in a degraded control response. In order to avoid such a problem, a rise in the voltage V is detected by the voltage comparator 6 so that the oxygen control device 7 supplies oxygen into the gas conduit 17 thereby to prevent control from entering into the electron conduction domain A shown by the hatched portion in FIG. 2, and at the same time, the current Io is reduced by the voltage limiter 11 so as to prevent a further rise in the voltage. In addition, if the voltage has reached the domain A, the voltage limiter 12 operates to discharge the electrolyte so as to prevent the voltage from further rising. Thus, the electrolyte 1 is protected from entering into the electron conductivity domain and the control response is enhanced. In case the control device 7 is a combustion device, such as a gasoline engine or Diesel engine, the exhaust gas from the engine is subjected to the measurement.

The setup current Io might become inconsistent with the oxygen concentration of gases due to the ageing of the diffusion resistance member or electrolyte, and in this case the value of Io needs to be corrected accurately. The correction for the value of Io is carried out in the following manner. First, the oxygen control device 7 is heated and gas of a known oxygen concentration is introduced through a pipe 7a into the conduit 17. Next, the current value Io corresponding to that known oxygen concentration is set by the current setting circuit 2. Consequently, a value V in the curve of FIG. 3 corresponding to the current Io is detected by the voltage measuring circuit 4. Then, the switch 13 is turned on and the current Io is set so that the voltage V coincides with Vo, and the value of Io at this time is the setup current corresponding to the oxygen concentration of gases under measurement. The current at this moment is for $P_V = O$, and Equation (2) is reduced to:

$$I_1 = \frac{Da \cdot 4F}{lRT} P_M \tag{3}$$

If calibration is carried out using atmospheric air which has an oxygen concentration of 21%, the value of Io should be set for a setting target of x% as:

$$Io = I_1 \times \frac{X}{21} \quad (4)$$

Then, the oxygen concentration can be controlled accurately even if the cross section a of the diffusion resistance member varies slightly due to dusts in gases. The value of $I_1$ is stored in the memory 14.

If I is set to zero in the arrangement of FIG. 1, Equation (1) is reduced to:

$$V = \frac{RT}{4F} \ln \frac{P_A}{P_V} \quad (5)$$

Figure 5:
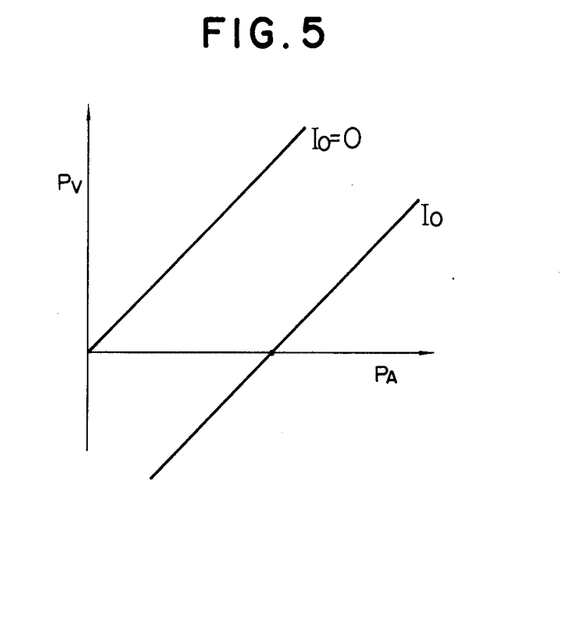

By controlling the device 7 so that the voltage V coincides with Vo, the oxygen concentration of gases can be controlled to a near-zero range to provide $P_V \approx O$ as shown in FIG. 5.

Figure 6:
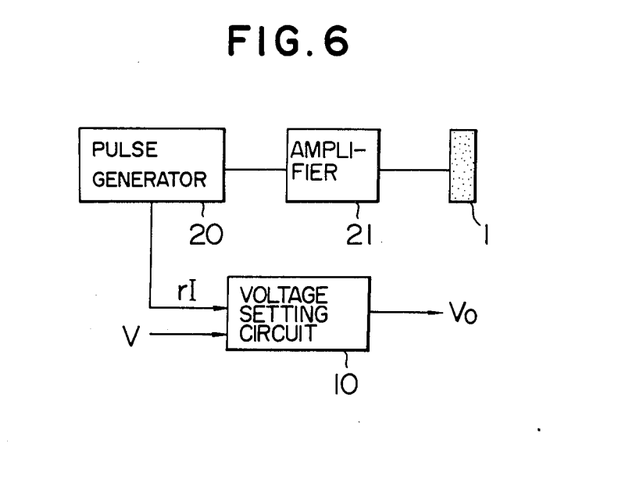
FIG. 6 is a block diagram showing one embodiment of the invention operating with a pulse voltage.

When the pulse current is used for the arrangement of FIG. 1, the current setting circuit 2 is arranged by use of a pulse generator 20 and an amplifier 21 as shown in FIG. 6, and the mean current I is supplied to the voltage setting circuit 10, whereby the oxygen concentration can be controlled to provide $P_V \approx O$. In this case, the mean current I can be varied by changing the duty cycle of pulses, and a higher control accuracy can be achieved for the case of a small current I.

Another embodiment of the invention will be described with reference to FIG. 7. A solid electrolyte 1 of the oxygen ion conduction type is connected to a current controller 25 and voltage controller 26 for controlling the current and voltage supplied to the electrolyte. The current and voltage are detected by a current sensor 27 and voltage sensor 28, respectively. The output signal from the current sensor 27 is fed to the first setting unit 29, arithmetic processing circuit 30 and second voltage setting circuit 10. The setting unit 29 provides the setting output, which depends on the detected current, to the voltage controller 26, and the setting output Vo of the voltage setting circuit 10 is supplied to a comparator 32. The comparator 32 also receives the output signal from the voltage sensor 28, and a current setting unit 33 controls the current controller 25 so that the comparator 32 provides zero output. The output of the comparator 32 is supplied to a pulse generator 34, and the output of a timer 35 is supplied to the arithmetic processing circuit 30.

Figure 7:
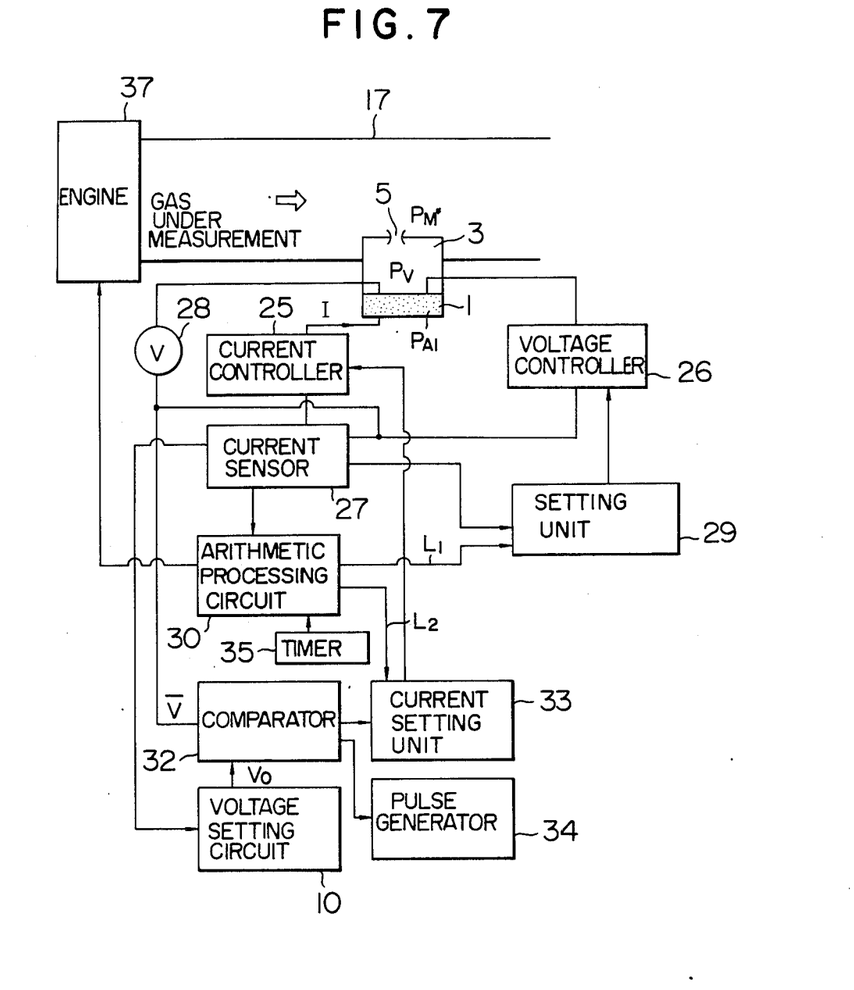
FIG. 7 is a block diagram showing another embodiment of the inventive oxygen concentration control system.

The current in the solid electrolyte 1 flows in the direction shown by the arrow in FIG. 7 so that oxygen in the chamber 3 is taken out of the chamber. An arrangement is made so that the electrolyte 1 is heated to a certain temperature at which it provides oxygen ion conduction.

When the partial pressure $P_V$ within the chamber 3 is substantially zero, the current $I_o$ is given by Equation (3). The voltage V is compared with the setup value Vo by the comparator 32, and the current I is controlled by the current setting unit 33 so that the voltage V coincides with Vo. The current $I = Io$ is detected by the current sensor 27 and indicted to the arithmetic processing circuit 30, and then the partial pressure $P_M$ corresponding to the oxygen concentration of gases can be detected. An internal combustion engine 37 which is the source of gases to be measured is controlled so that the detected partial pressure $P_M$ is equal to the specified value.

The following describes the operations in various cases:
(a) the voltage V is varied, (b) the current I is varied, (c) the air excess factor λ is less than 1, and (d) $P_A$ is equal to $P_M$.

(a) Variable Voltage

Figure 8:
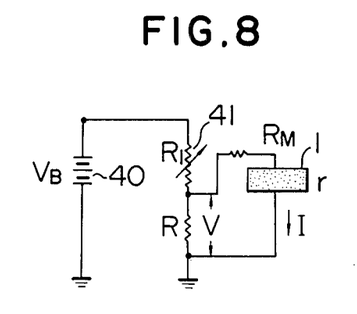
FIG. 8 is a schematic diagram for explaining the principle of the embodiment shown in FIG. 7.

In case the voltage controller 26 is made up of a battery 40, resistor 41, etc. as shown in FIG. 8, the voltage applied to the electrolyte 1 can be varied. The voltage V vs. resistance $R_1$ relationship is given by the following equation.

$$V = \frac{V_B - R_1 I}{1 + \frac{R_1}{R}} \quad (6)$$

where $V_B$ is the terminal voltage of the battery 14.

Assuming the electrolyte 1 to have the resistance r, Equation (6) is reduced to:

$$V = \frac{V_B}{1 + \frac{R_1}{R + r}} \quad (7)$$

Figure 9:
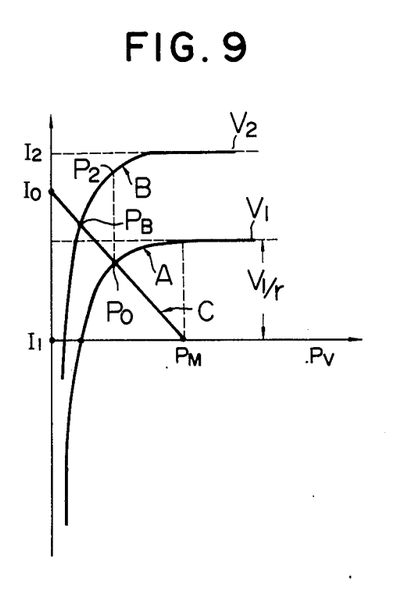
FIG. 9 is a graphical representation showing the operation of the embodiment shown in FIG. 7.
Figure 10:
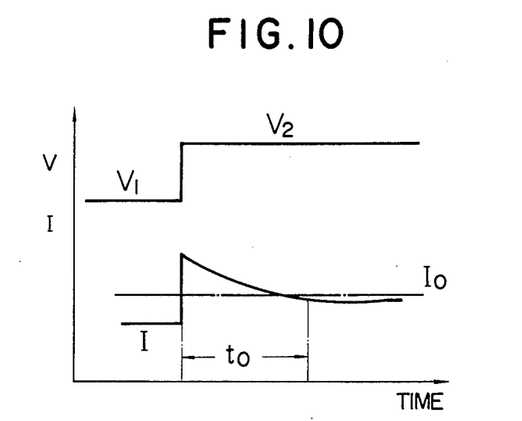
FIGS. 10 and 11 are waveform charts for explaining a technical subject encountered by the present invention.
Figure 11:
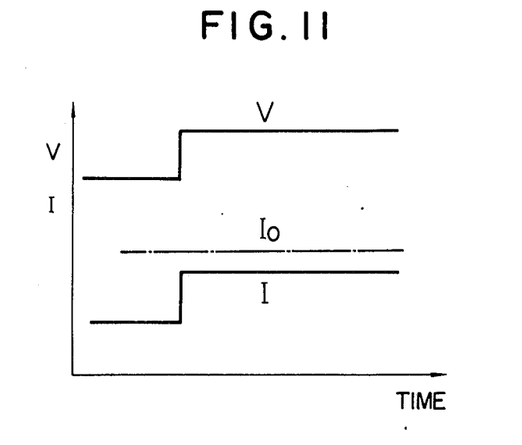

If the value of $R_1$ is made small, the values of V and I increase, and when $P_V$ of the electrolyte 1 falls, the electromotive force in the second term on the right side of Equation (1) increases and the current no longer increases along with increasing V. FIG. 9 shows the relationship of Equation (1) with the voltage V being set to a constant. The curve A shows the case of $V = V_1$, while the curve b shows the case of $V = V_2$ ($V_2 > V_1$) and the current approaches $I = V/r$ when $P_V$ is large. The curve C in FIG. 9 shows the relationship of Equation (2), indicating $P_V = P_M$ for $I = O$, and $I = Io$ for $P_V = O$. The partial pressure $P_V$ equals $P_M$ when $I = O$, and if $R_1$ is reduced to provide $V = V_1$, the circuit of FIG. 7 operates so that the current balances at the intersection Po of the curves A and C. Accordingly, if the voltage is increased to $V = V_2$, the current will balance at $P_B$. If the value of $R_1$ is varied discontinuously to bring V from $V_1$ to $V_2$, it takes time for $P_V$ within the chamber 3 to fall, and, in FIG. 9, the current once increases to point P then the current I is reduced to $P_B$ along with the falling $P_V$. FIG. 10 shows the nature of this operation. FIG. 11 shows the case where the rise of V is small and the current I does not vary with respect to time.

As can be understood from FIGS. 7 and 9, when the V is made large enough, i.e., $V \approx Vo$, the current I approaches Io, and by detecting the current by the current sensor 27, the pressure $P_M$, i.e., the oxygen concentration can be measured. The internal combustion engine 37 is controlled so that the value of $P_M$ is equal to the setup value.

The value of $P_V$ at the balanced point becomes small as the value of V is increased as can be seen from FIG. 9. However, as shown in FIG. 2, if V rises over 1.0 volt, electron conduction occurs and Equation (3) is no longer satisfied, and if V is too low, the current I does not balance and the current Io cannot be measured. The proper setup voltage Vo for the setting circuit 10 is around:

$$Vo = rI + (0.1 \text{ to } 1.0) \ldots \quad (8)$$

And, if the current I is increased, it is desirable to raise the voltage Vo proportionally. Signal I from the current sensor 27 is supplied to the setting unit 29, and the voltage of the voltage controller 26 is controlled so that V equals Vo. The current Io at this moment is detected by the current sensor 27 and fed to the arithmetic processing circuit 30 thereby to obtain the value of $P_M$ using the relationship of Equation (3).

When the application voltage to the electrolyte 1 is removed in the condition of $P_V \approx O$ inside the chamber 3, the second term on the right side of Equation (1) exhibits an electromotive force of around 1 volt, and an inverse current will flow in the current measuring resistor $R_M$ in FIG. 8. At this time, the $P_V$ approaches gradually $P_M$, the partial pressure electromotive force falls gradually to zero, and the inverse current decreases to zero. When the current controller 25 starts to supply the current to the electrolyte 1, $P_V$ does not balance for a period of $t_o$ shown in FIG. 10 from that starting moment, and the current Io is not in correspondence to $P_M$. On this account, this embodiment includes a timer 35 in the arithmetic processing circuit 30 so that the signals for controlling the fuel and air for the internal combustion engine 37 are not outputted for a duration of $t_o$. This process may be carried out in such a way that the output of the current sensor 27 is fed through an A/D converter to a microprocessor, and a point of time at which the voltage V or current I varies sharply or exceeds a certain level is detected, so that the timer associated with the microprocessor is activated at that point of time. Thus, malfunctioning of the control system can be prevented by provision of a means for neglecting the output signal from the current sensor 27 as a control signal for determining the amount of fuel and air during the period $t_o$ following the application of the current to the electrolyte 1 to the setting of the current.

At the balanced point of $P_B$ in FIG. 9, if $P_M$ increases, the curve C moves upward, and accordingly, the I increases along with the current rising $P_V$, thus suppressing the increase of $P_V$.

The oxygen partial pressure within the chamber 3 does not fall completely to zero in general. In case of measuring combustion gases, carbon dioxide dissociates in the reaction:

$$CO_2 \rightleftharpoons CO + \tfrac{1}{2} O_2 \ldots \quad (9)$$

And, oxygen of about $P_V = 10^{-12}$ remains in the chamber 3. Accordingly, when V is set to 0.5 volt with $P_V = 10^{-12}$ and $P_M = 10^{-12}$, the voltage V and the electromotive force balance to cause I=O as shown in FIG. 9. At this time, if the V is increased, I increases and $P_V$ decreases. However, the reaction of Equation (9) proceeds rightwardly, preventing a decrease of $P_V$ within the chamber 3, and the current I is not $I_1$ shown in FIG. 12, but is likely to be $I_2$ because of the dependency to the reaction speed of Equation (9).

Figure 12:
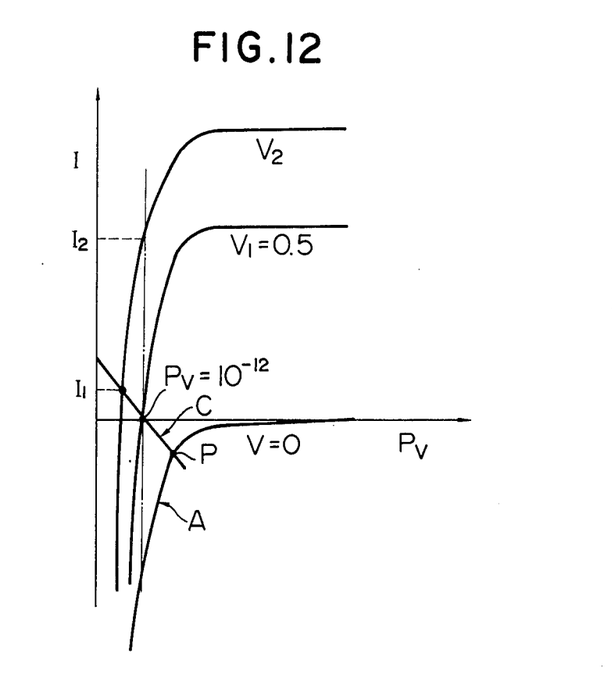
FIGS. 12 and 14 are graphical representations for explaining the operation of the arrangement shown in FIG. 7.

In case of V=O, on the other hand, the relationship of Equation (1) is plotted to curve A in FIG. 12, i.e., I is negative, and oxygen is transferred through electrolyte 1 into the chamber 5. When the $P_V$ becomes substantially zero, a current corresponding to the electromotive force of 0.5 volt flows inversely through the external impedance element 5. By this current, oxygen is transferred into the chamber 3, causing $P_V > P_M$, and the curves C and A are balanced at the intersection P.

Figure 13:
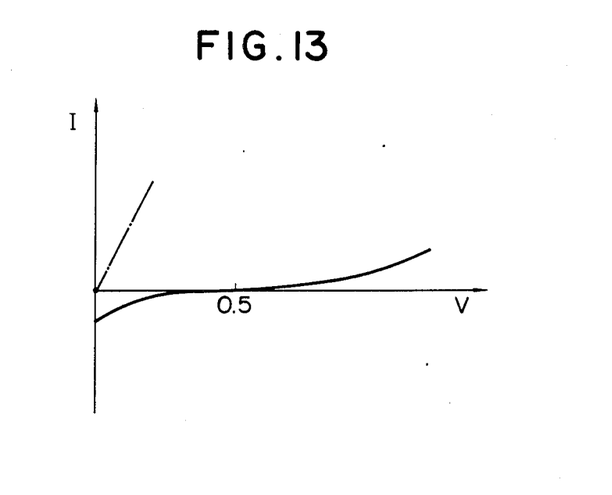

The relationship of V and I for $P_M = 10^{-12}$ is shown in FIG. 13, and if the voltage is set with the relationship of Equation (8), the error caused by the dissociation of $CO_2$ can be avoided. For $r = 20\Omega$, the voltage V will vary in the range of 0 to 1 volt in response to the variation of $P_V$, and the current I will vary in the range of 0 to 50 mA.

As described above, in measuring Io by using the current sensor 27, the current Io will be small for a small $P_M$ as shown in Equation (3). If Io=40 mA for the oxygen concentration of 21%, Io will be 4 mA for the concentration of 2.1%, and high precision measurement is required. In this case, a pulse current is supplied to the electrolyte 1, and the $P_M$ can be obtained from the value of duty cycle of the pulse current.

Figure 14:
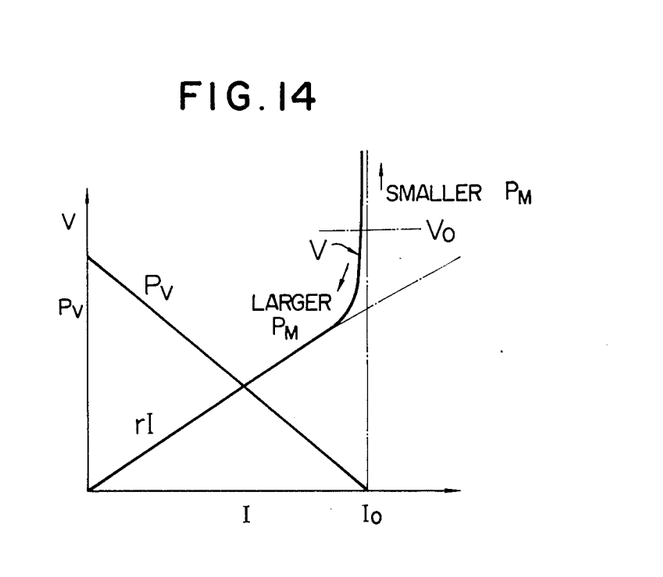

The signal V from the voltage sensor 28 is supplied to the comparator 32, and the current is set by the current setting unit 33 so that the voltage V coincides with the setup value Vo. The current controller 25 is controlled, and the current is measured by the current sensor 27, and the signal corresponding to $P_M$ is obtained. Since the signal V is raised by the amount of rI by the current flowing in the electrolyte 1 having a resistance of r, the current I is fed to the setting unit 10 so that Vo is varied depending on the value of I. When $P_M$ increases as shown in FIG. 14, $P_V$ increases, and the voltage V is prevented from failing by increasing the current I. Conversely, if $P_M$ falls, $P_V$ decreases, and the voltage V is prevented from rising by decreasing the I. When current $P_M$ is small, the current I has a small value, and the current I may be given as a duty cycle signal in order to enhance the measurement accuracy.

Figure 15:
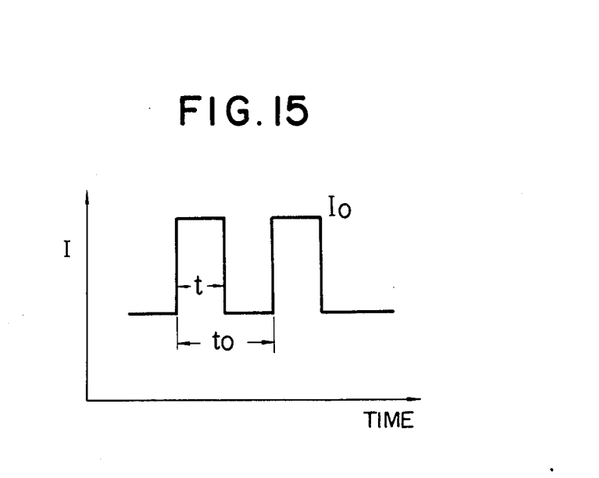
FIG. 15 is a waveform chart explaining the application of the pulse voltage to the electrolyte.

As shown in FIG. 15, the duty cycle $t/t_o$ of the pulse current I is varied so that V equals Vo, and $P_M$ can be detected by measuring the pulse width t. That is, a pulse generator 34 is used, and $P_M$ can be detected by varying the pulse width t or the period $t_o$ by the output signal of the comparator 32. For example, assuming the oxygen concentration to be 21% for a duty cycle of $t/t_o = 100\%$, the oxygen concentration for $t/t_o = 1\%$ will be 0.21%. The voltage V is varied in proportion to the variation of I, and the input voltage to the comparator, i.e., the rI component, is averaged as can be understood from Equation (1).

(b) Variable Current

When the current I in the electrolyte 1 is increased by the current controller 26, the voltage V increases for a constant $P_V$ according to Equation (1) as shown in FIG. 14. On the other hand, if $P_V$ falls to approximately zero by the increase of I, the voltage V will increase. Accordingly, the $P_M$ can be obtained by measuring the current I=Io at a point where the voltage varies sharply in response to the variation of the current.

Also in this case, it takes a time of $t_o$ before $P_V$ balances for the variation of the current I in the neighborhood of Io, and therefore a timer function is provided so that the signal from the voltage sensor 3 is not used for controlling the fuel and air for the combustion engine 37 during this period.

If Io is fixed in FIG. 14, a slight increase in $P_M$ causes an increase of $P_V$, and the voltage V will fall largely. Conversely, a slight decrease in $P_M$ causes a decrease of $P_V$, and the voltage V will increase largely. The value of V is given to the microprocessor, and the air and fuel metering devices are adjusted so that the voltage V is constant, whereby the oxygen concentration of gases under measurement can be kept constant.

(c) Air Excess Factor λ Less Than 1

Although an air excess factor λ of less than one results in a small $P_M$, the oxygen concentration does not reach zero because of the reaction of Equation (9). In FIG. 12, if $P_M$ is small, the curve C moves leftward, and current I becomes negative for a constant V. If the current I is fixed to zero, the voltage V rises as $P_M$ decreases.

When gases have an air excess factor of less than one, the electromotive force increases. The electromotive force increases as the factor λ decreases, and the inverse current flowing in the external impedance element 5 increases. Consequently, oxygen is supplied from the outside into the chamber 3, and it is used for oxidizing carbon monoxide. In this case, if a voltage V is applied, the electrolyte 1 lacks oxygen, exhibiting electron conduction, and the current is restored to positive. Thus, when gases under measurement are in the state of λ<1, the arithmetic processing circuit 30 bolts the control for providing V=0.5 volt on the setting units 29 and 33 through lines L1 and L2 and retains the current I at zero, so as to prevent the failure of control caused by electron conduction. When setting is made to the state of λ>1, the system enters the operation with V=constant.

In FIG. 12, if the current Io is zero, the voltage V is equal to the electromotive force, and by controlling the fuel and air metering devices so as to maintain a constant voltage V, gases under measurement are controlled to the state of λ=1. If the current Io is made negative, the oxygen partial pressure $P_V$ within the chamber 3 increases and balances at the point:

$$|I| = \frac{Da \cdot 4F}{lRT}(P_V - P_M) \quad (10)$$

In case current I is constant, if value of the $P_M$ decreases, i.e, λ decreases, $P_V$ decreases and the voltage V rises. On the other hand, if $P_M$ increases, $P_V$ increases and the V falls. However, the voltage current value I is generally small, and for gases with λ<1, malfunctioning of the control system can be prevented by controlling the fuel and air metering devices in open-loop operation, or by controlling the devices on a closed loop basis in the negative range of the current I.

Thus, for restoring the gas state of λ>1 from the state of λ<1, the current is set to positive value.

At this time, diffusion of oxygen into the chamber 3 has a time lag, and an increase of the current I causes a temporary, sharp fall pressure in the $P_V$, resulting in a rise in the voltage V, and a signal indicating the lack of oxygen is produced even if the excess air factor λ of the gases is controlled normally in the open loop mode. In such a case, an integrator is added to the current setting unit 33 so that the current I increases gradually, and malfunctioning of control can be prevented. Alternatively, the closed loop operation is halted during the settling period $t_o$. In reducing the air excess factor λ, the pressure $P_V$ in the chamber 3 increases temporarily, and also in this case, malfunctioning of the control can be prevented by a similar method.

In controlling the current I so as to maintain the voltage V constant, when the excess air factor λ decreases, the voltage V increases, and therefore, the current I is reduced to maintain the voltage V constant. The response of current I to the variation of λ has a time lag due to the volume of the chamber 3, and it is desirable to select proper closed loop gain for the current setting unit 11. For a rapid change of λ, the P and I gains should be increased so as to achieve quick settling. For enhancing the control stability, the gains are lowered so as to prevent malfunctioning of the control system.

(d) $P_A = P_M$

The following describes the case where the oxygen partial pressure $P_A$ outside the electrolyte 1 is equal to $P_M$, i.e., the exterior wall of the chamber 3 is exposed to gases under measurement. The arragement of the oxygen concentration sensor will be described in connection with FIG. 16.

Figure 16:
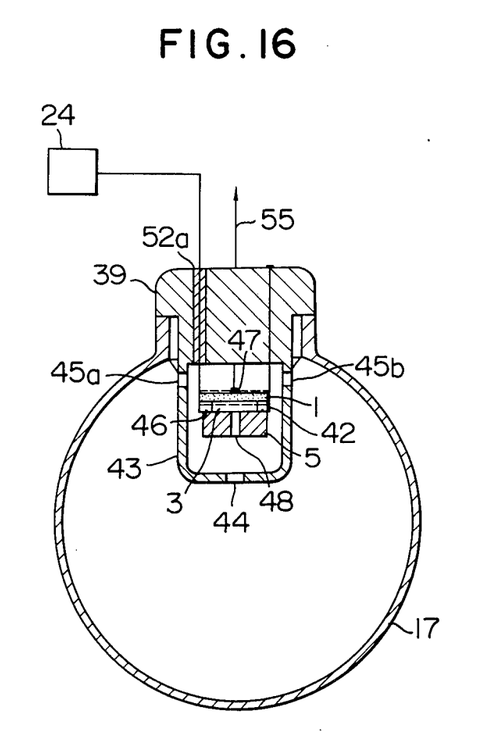
FIG. 16 is a cross-sectional view showing the structure embodied by the present invention.

In FIG. 16, the measurement gas conduit 17 is provided with a member 39 with a cover 43, on which are provided an exhaust gas in-port 44 and exhaust gas out-ports 45a and 45b. The porous solid electrolyte 1 is provided inside the cover 43, and platinum electrodes 47 are disposed on both sides of the electrolyte 1. In the lower portion of the solid electrolyte 1 on the drawing, there is mounted through a spacer ring 42 a diffusion resistance member 5 made of ceramic with an orifice 48 formed therein. The resistance member 5 has a lead wire 46 for a heating resistor 49 (not shown), with one end of the lead wire 46 being led out through an insulator 52 to a heater circuit 24, and with another end being grounded. The solid electrolyte 1 and diffusion resistance member 5 are fixed together with heat resisting adhesive (e.g., glass or ceramic) within the chamber 3 and hung by the lead wire 46 inside the cover 43, and they can be kept at a high temperature by a small heating source. The electrodes 47 provided on both sides of the electrolyte 1 are conducted through a lead wire 55 to the current controller 25, voltage controller 26 and voltage sensor 28 in FIG. 7.

Figure 17:
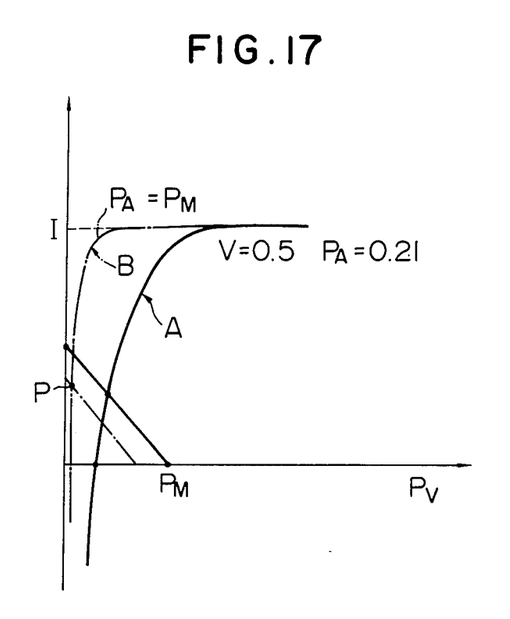
FIGS. 17 and 18 are graphical representations for explaining the operation of the embodiment shown in FIG. 17.

As shown in FIG. 17, if $P_A$ and $P_M$ have small values for the curve A of $P_A = 0.21$, the curve is reduced to curve B. That is, balance is made at point P with smaller $P_V$. When the parameters approach λ=1, the electromotive force decreases. When the current is zero, the voltage V becomes zero as given by Equation (2).

Figure 18:
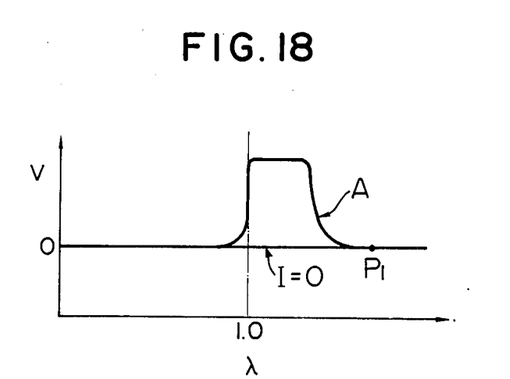

In the case of I=0, $P_A$ equals $P_M$, and the electrolyte 1 has an equal oxygen concentration on both sides, causing no oxygen ions to move. Accordingly, the voltage is zero irrespective of the value of λ as shown in FIG. 18.

In the case of I≠0, the second term on the right side of equation (1), i.e., $E = \ln P_A/P_V$, can be expressed as:

$$E = \ln \frac{P_M}{P_M - k_1} \quad (11)$$

If $P_M$ is larger than $k_1$, E becomes zero, and if $P_M$ approaches $k_1$, the value of E increases. The value of $P_V$ does not become zero or negative even if $P_M$ becomes smaller than $k_1$, and for $P_M < K_1$, the dissociation of carbon dioxide takes place as shown by Equation (9) and a fall in $P_V$ is prevented. For λ≦1, on the other hand, $P_V$ due to dissociation of oxygen coincides with $P_M$, and the second term on the right side of Equation (1) varies as shown by curve A in FIG. 18.

If the status changes from the domain of λ>1 to the domain of λ<1, oxygen within the chamber 3 is excessive at point $P_1$ of FIG. 12, causing a momentary $P_A$ to become smaller than $P_V$, and the voltage V becomes negative. Therefore, for the case of $P_A = P_M$, there are two points of λ which satisfy V=0.5 volt, and the control system is prone to malfunction.

Therefore, the use of the signal V for controlling air and fuel is suspended during the settling period of $P_V$. Also in the case of λ≦1, the use of the signal V is suspended so as to prevent malfunctioning of the control system.

According to the present invention, the control operation is halted if the correspondence between the oxygen concentration of gases under measurement and the output signal of the sensor is lost, whereby the control system is stabilized effectively. The amount of oxygen can be controlled so as to maintain the proper voltage, whereby deterioration of response due to electron conduction can be prevented.

The present invention achieves a similar effect for the system wherein oxygen within the chamber is evacuated by a constant current and the oxygen concentration is measured from the variation of oxygen concentration within the chamber with respect to time.

We claim:

1. An oxygen concentration control system comprising:
    an electrolyte of oxygen ion conductivity type, having one surface exposed to gases under measurement which are supplied thereto through a diffusion resistance member;
    current supply means for continuously supplying to said electrolyte an electric current having a predetermined value corresponding to a selected oxygen concentration;
    voltage detection means for detecting the voltage produced across said electrolyte by said electric current of predetermined value;
    means for generating a predetermined reference voltage having a magnitude which resides within a range of values of said voltage detected by said voltage detection means between a predetermined lower limit and an upper limit where the electrolyte begins to pass into an electron conduction state;
    means for reducing the current supplied to said electrolyte if said voltage detected by said voltage detection means is so large that electron conduction occurs; and
    control means responsive to said detected voltage and said reference voltage for controlling the oxygen concentration of said gases under measurement to suppress a variation of said voltage detected by said voltage detection means when said detected voltage is of different value than said reference voltage.

2. A control system according to claim 1, wherein said control means comprises a comparator which compares said detected voltage with said reference voltage and provides a control signal if said detected voltage is higher than said reference voltage, and means for supplying oxygen to said gases under measurement in accordance with said control signal from said comparator.

3. A control system according to claim 2, wherein said control means further comprises an integrator which integrates the output signal from said comparator, an output signal from said integrator being supplied as a control signal to said oxygen supply means.

4. A control system according to claim 3, further including means for varying the time constant of said integrator depending on the flow rate of gases under measurement.

5. A control system according to claim 1, wherein said reducing means further comprises means for limiting the current supplied from said current supply means to said electrolyte.

6. A control system according to claim 1, further comprising voltage limiting means connected across said electrolyte for limiting the voltage across said electrolyte to a predetermined voltage level.

7. A control system according to claim 1, wherein said reference voltage generating means comprises means for generating a reference voltage having a magnitude which varies in proportion to the magnitude of the current supplied from said current supply means to said electrolyte.

8. A control system according to claim 1, wherein said current supply means comprises means for supplying an electric current whose predetermined magnitude is controlled by an externally-applied control signal.

9. A control system according to claim 8, wherein said control means comprises:
    means including a comparator for comparing said detected voltage with said reference voltage;
    means for supplying gases of known oxygen concentration instead of gases under measurement to said electrolyte through said diffusion resistance member; and memory means for storing the magnitude of the current from said current supply means at a time when said comparator detects coincidence between the voltages supplied to its inputs, a target current value for obtaining a predetermined oxygen concentration being set in accordance with the current value stored in said memory means.

10. A control system according to claim 1, wherein said current supply means comprises means for generating a pulse current with a variable duty cycle.

11. An oxygen concentration control system comprising:
    an electrolyte of oxygen ion conductivity type, having one surface exposed to gases under measurement which are supplied thereto from a source of gases through a diffusion resistance member;
    means for creating a voltage between both surfaces of said electrolyte by supplying electric current thereto;
    voltage detection means for detecting the voltage produced across said electrolyte;
    means for generating a predetermined reference voltage having a magnitude which resides within a range of values of the voltage detected by said voltage detection means between a predetermined lower limit and an upper limit where the electrolyte begins to pass into an electron conduction state;
    control means reponsive to said detected voltage and said reference voltage for controlling the amount of electric current supplied to said electrolyte so that the voltage detected by said voltage detection means coincides with said reference voltage;
    means for detecting a current flowing in said electrolyte;
    means responsive to said current detecting means for controlling the oxygen concentration in the gases under measurement until the current detected by said current detection means has a value corresponding to a predetermined oxygen concentration; and
    means for halting the control operation of said electric energy control means when the electric energy supplied to said electrolyte is so large that electron conduction occurs.

12. A control system according to claim 11, wherein said halting means comprises a timer which starts operating in response to said large variation of electric energy, counts a predetermined time period, and halts the control operation of said gas source control means during said counting period.

* * * * *